US011053299B2

(12) United States Patent
Soon-Shiong et al.

(10) Patent No.: US 11,053,299 B2
(45) Date of Patent: Jul. 6, 2021

(54) SUPERKINE (71) Applicants: Immunity Bio, Inc., Culver City, CA (US); Altor Bioscience, LLC, Miramar, FL (US)

(72) Inventors: Patrick Soon-Shiong, Culver City, CA (US); Hing C. Wong, Weston, FL (US); Peter Rhode, Miami, FL (US); Bai Liu, Cooper City, FL (US); Xiaoyun Zhu, Weston, FL (US); Kai-Ping Han, Weston, FL (US)

(73) Assignee: IMMUNITY BIO, INC., Culver City, CA (US)

( * ) Notice: Subject to any disclaimer, the term of this patent is extended or adjusted under 35 U.S.C. 154(b) by 0 days.

(21) Appl. No.: 16/442,265

(22) Filed: Jun. 14, 2019

(65) Prior Publication Data

US 2019/0330309 A1  Oct. 31, 2019

Related U.S. Application Data (63) Continuation-in-part of application No. 15/951,042, filed on Apr. 11, 2018, now Pat. No. 10,899,821, which is a continuation of application No. 15/083,998, filed on Mar. 29, 2016, now Pat. No. 10,150,805, which is a continuation of application No. 13/854,903, filed on Apr. 1, 2013, now Pat. No. 9,328,159, which is a continuation of application No. 13/769,179, filed on Feb. 15, 2013, now Pat. No. 9,255,141, which is a continuation-in-part of application No. 13/238,925, filed on Sep. 21, 2011, now Pat. No. 8,507,222, application No. 16/442,265, filed on Jun. 14, 2019, which is a continuation-in-part of application No. PCT/US2017/066449, filed on Dec. 14, 2017.

(60) Provisional application No. 61/527,911, filed on Aug. 26, 2011, provisional application No. 61/384,817, filed on Sep. 21, 2010, provisional application No. 62/434,389, filed on Dec. 14, 2016.

(51) Int. Cl.
| C07K 14/715 | (2006.01) |
| C12N 15/62 | (2006.01) |
| C12P 21/00 | (2006.01) |
| C07K 16/18 | (2006.01) |
| A61K 39/395 | (2006.01) |
| C07K 14/54 | (2006.01) |
| A61K 38/20 | (2006.01) |
| C12N 15/09 | (2006.01) |
| A61K 38/17 | (2006.01) |
| A61K 45/06 | (2006.01) |
| C07K 16/28 | (2006.01) |
| A61K 38/00 | (2006.01) |

(52) U.S. Cl.
CPC ...... *C07K 14/7155* (2013.01); *A61K 38/1793* (2013.01); *A61K 38/2086* (2013.01); *A61K 39/3955* (2013.01); *A61K 45/06* (2013.01); *C07K 14/5443* (2013.01); *C07K 16/18* (2013.01); *C07K 16/2887* (2013.01); *C12N 15/09* (2013.01); *C12N 15/62* (2013.01); *C12P 21/00* (2013.01); *A61K 38/00* (2013.01); *C07K 2317/622* (2013.01); *C07K 2317/732* (2013.01); *C07K 2319/00* (2013.01); *C07K 2319/21* (2013.01); *C07K 2319/22* (2013.01); *C07K 2319/30* (2013.01)

(58) Field of Classification Search
CPC .................................................. C07K 14/7155
See application file for complete search history.

(56) References Cited

U.S. PATENT DOCUMENTS

| 5,116,964 A | 5/1992 | Capon et al. |
| 5,541,087 A | 7/1996 | Lo et al. |
| 5,620,939 A | 4/1997 | Halasa et al. |
| 6,344,192 B1 | 2/2002 | Grooten et al. |
| 8,124,084 B2 | 2/2012 | Lefrancois et al. |
| 8,163,879 B2 | 4/2012 | Wong et al. |
| 8,492,118 B2 | 7/2013 | Wong et al. |
| 8,507,222 B2 | 8/2013 | Wong et al. |
| 8,940,288 B2 | 1/2015 | Lefrancois et al. |
| 8,940,289 B2 | 1/2015 | Wong et al. |
| 9,255,141 B2 | 2/2016 | Wong et al. |
| 9,328,159 B2 | 5/2016 | Wong et al. |
| 9,365,630 B2 | 6/2016 | Lefrancois et al. |
| 9,428,573 B2 | 8/2016 | Wong et al. |
| 9,464,127 B2 | 10/2016 | Wong et al. |

(Continued)

FOREIGN PATENT DOCUMENTS

| AU | 2008253720 B2 | 1/2014 |
| AU | 2013273643 B2 | 1/2016 |

(Continued)

OTHER PUBLICATIONS

Yu et al. (Dec. 15, 2010, e-Published (Oct. 5, 2010) "Simultaneous Blockade of Multiple Immune System Inhibitory Checkpoints Enhances Antitumor Activity Mediated by Interleukin-15 in a Murine Metastatic Colon Carcinoma Model", Clinical Cancer Research, 16(24):1-16 pages.

(Continued)

*Primary Examiner* — Prema M Mertz
(74) *Attorney, Agent, or Firm* — Mintz, Levin, Cohn, Ferris, Glovsky and Popeo, P.C (57) ABSTRACT

Contemplated compositions and methods comprise chimeric molecule complexes that advantageously provide activating signaling to immune competent cells when bound to ALL cells. Furthermore, chimeric molecule complexes include an Fc portion to extend serum half live time and facilitate purification.

18 Claims, 2 Drawing Sheets

(56) References Cited

U.S. PATENT DOCUMENTS

| | | |
|---|---|---|
| 9,593,152 B2 | 3/2017 | Wong et al. |
| 9,925,247 B2 | 3/2018 | Liu et al. |
| 10,150,805 B2 | 12/2018 | Wong et al. |
| 10,358,478 B2 | 7/2019 | Wong et al. |
| 10,450,359 B2 | 10/2019 | Wong et al. |
| 10,537,615 B2 | 1/2020 | Liu et al. |
| 2003/0144474 A1 | 7/2003 | Weidanz et al. |
| 2003/0180888 A1 | 9/2003 | Fraser |
| 2004/0156826 A1 | 8/2004 | Dangond et al. |
| 2004/0242025 A1 | 12/2004 | Angerpointner et al. |
| 2004/0253587 A1 | 12/2004 | Grabstein et al. |
| 2006/0263857 A1 | 11/2006 | Lefrancois et al. |
| 2009/0010966 A1 | 1/2009 | Davis et al. |
| 2009/0117618 A1 | 5/2009 | Herrmann et al. |
| 2009/0324538 A1 | 12/2009 | Wong et al. |
| 2010/0278774 A1 | 11/2010 | Wong et al. |
| 2012/0177595 A1 | 7/2012 | Wong et al. |
| 2012/0230946 A1 | 9/2012 | Wong et al. |
| 2013/0121960 A1 | 5/2013 | Sadelain et al. |
| 2014/0099254 A1 | 4/2014 | Chang et al. |
| 2014/0134128 A1 | 5/2014 | Wong et al. |
| 2014/0205560 A1 | 7/2014 | Wong et al. |
| 2014/0219955 A1 | 8/2014 | Wong et al. |
| 2014/0242025 A1 | 8/2014 | Wong et al. |
| 2015/0023938 A1 | 1/2015 | Yee |
| 2015/0132257 A1 | 5/2015 | Wong et al. |
| 2016/0213750 A1 | 7/2016 | Wong et al. |
| 2016/0355567 A1 | 12/2016 | Wong et al. |
| 2016/0367635 A1 | 12/2016 | Wong et al. |
| 2017/0088597 A1 | 3/2017 | Wong et al. |
| 2019/0023766 A1 | 1/2019 | Wong et al. |
| 2020/0016239 A1 | 1/2020 | Liu et al. |
| 2020/0140513 A1 | 5/2020 | Wong et al. |
| 2020/0181237 A1 | 6/2020 | Wong et al. |
| 2020/0190164 A1 | 6/2020 | Wong et al. |
| 2021/0030844 A1 | 2/2021 | Liu et al. |

FOREIGN PATENT DOCUMENTS

| | | |
|---|---|---|
| AU | 2011305476 B2 | 12/2016 |
| AU | 2016326575 A1 | 4/2018 |
| AU | 2017201056 B2 | 12/2018 |
| AU | 2015284248 B2 | 4/2020 |
| CA | 2811734 A1 | 3/2012 |
| CA | 2953816 A1 | 1/2016 |
| CA | 2999294 A1 | 3/2017 |
| CA | 2690825 C | 2/2019 |
| CN | 1441675 A | 9/2003 |
| CN | 1478098 A | 2/2004 |
| CN | 1493687 A | 5/2004 |
| CN | 1760209 A | 4/2006 |
| CN | 1780856 A | 5/2006 |
| CN | 1942481 A | 4/2007 |
| CN | 101360827 A | 2/2009 |
| CN | 101484472 A | 7/2009 |
| CN | 101743249 A | 6/2010 |
| CN | 104672325 A | 6/2015 |
| CN | 105017429 A | 11/2015 |
| CN | 106659775 A | 5/2017 |
| CN | 101743249 B | 8/2017 |
| CN | 103370339 B | 12/2017 |
| CN | 104109200 B | 3/2018 |
| CN | 107880136 A | 4/2018 |
| CN | 108463239 A | 8/2018 |
| CN | 108948177 A | 12/2018 |
| EP | 0971728 A1 | 1/2000 |
| EP | 1777294 A1 | 4/2007 |
| EP | 1934353 A2 | 6/2008 |
| EP | 2160401 A1 | 3/2010 |
| EP | 2388266 A2 | 11/2011 |
| EP | 2537933 A1 | 12/2012 |
| EP | 2619229 A2 | 7/2013 |
| EP | 2388266 B1 | 4/2014 |
| EP | 2769984 A1 | 8/2014 |
| EP | 2160401 B1 | 9/2014 |
| EP | 2918607 A1 | 9/2015 |
| EP | 2619229 B1 | 4/2016 |
| EP | 3160498 A2 | 5/2017 |
| EP | 2769984 B1 | 8/2017 |
| EP | 2918607 B1 | 11/2017 |
| EP | 3305805 A1 | 4/2018 |
| EP | 3327040 A1 | 5/2018 |
| EP | 3352779 A1 | 8/2018 |
| EP | 3673915 A1 | 7/2020 |
| JP | H06-87898 A | 3/1994 |
| JP | H09-512165 A | 12/1997 |
| JP | H11-500908 A | 1/1999 |
| JP | 2001-502521 A | 2/2001 |
| JP | 2008-545397 A | 12/2008 |
| JP | 2009-512433 A | 3/2009 |
| JP | 2010-527919 A | 8/2010 |
| JP | 6251570 B2 | 9/2011 |
| JP | 2013-541335 A | 11/2013 |
| JP | 5501222 B2 | 3/2014 |
| JP | 2014524737 A | 9/2014 |
| JP | 5841623 B2 | 11/2015 |
| JP | 6152156 B2 | 6/2017 |
| JP | 2017-521410 A | 8/2017 |
| JP | 2018-046831 A | 3/2018 |
| JP | 6408039 B2 | 10/2018 |
| JP | 2018-174697 A | 11/2018 |
| JP | 2018-532729 A | 11/2018 |
| JP | 2019-033754 A | 3/2019 |
| KR | 10-2007-0000252 A | 1/2007 |
| KR | 10-2007-0002052 A | 1/2007 |
| KR | 10-2014-0020228 A | 2/2014 |
| KR | 10-2017-0047221 A | 5/2017 |
| KR | 10-2018-0125435 A | 11/2018 |
| KR | 102070098 | 1/2020 |
| MX | 2017000116 A | 5/2017 |
| WO | 94/04689 A1 | 3/1994 |
| WO | 94/29350 A2 | 12/1994 |
| WO | 95/27722 A1 | 10/1995 |
| WO | 96/26274 A1 | 8/1996 |
| WO | 96/32478 A1 | 10/1996 |
| WO | 97/34631 A1 | 9/1997 |
| WO | 97/41232 A1 | 11/1997 |
| WO | 98/36768 A1 | 8/1998 |
| WO | 0187330 A2 | 11/2001 |
| WO | 2005/046449 A2 | 5/2005 |
| WO | 2005/085282 A1 | 9/2005 |
| WO | 2006/063974 A2 | 6/2006 |
| WO | 2007/001677 A2 | 1/2007 |
| WO | 2007/046006 A2 | 4/2007 |
| WO | 2008/143794 A1 | 11/2008 |
| WO | 2009/002562 A2 | 12/2008 |
| WO | 2009/117117 A1 | 9/2009 |
| WO | 2012/040323 A2 | 3/2012 |
| WO | 2012/175222 A1 | 12/2012 |
| WO | 2013/076183 A1 | 5/2013 |
| WO | 2014/028776 A1 | 2/2014 |
| WO | 2014/066527 A2 | 5/2014 |
| WO | 2016/004060 A2 | 1/2016 |
| WO | 2017/053649 A1 | 3/2017 |
| WO | 2017/205726 A1 | 11/2017 |

OTHER PUBLICATIONS

Database UNIPROT (2004) "Sequence, retrieved from EBI, Database Accession No. Q6B416", XP002659761, 1 page.
Database UNIPROT (2002) "Sequence, retrieved from EBI, Database Accession No. Q8SPYO,", XP002659760, 1 page.
Davis (1998) "Ligand Recognition by Alpha Beta T Cell Receptors", Annual Reviews Immunology, 16:523-544.
Davis (1985) "Molecular Genetics of the T Cell-receptor Beta Chain", Annual Review of Immunology, 3:537-560.
Davis et al. (Aug. 4, 1988) "T-cell Antigen Receptor Genes and T-cell Recognition", Nature, 334(6181):395-402.
Deer et al. (2004) "High-Level Expression of Proteins in Mammalian Cells Using Transcription Regulatory Sequences from the Chinese Hamster EF-1α Gene", Cell Culture and Tissue Engineering, 20(3):880-889.

(56) References Cited

OTHER PUBLICATIONS

Doerks et al. (Jun. 1998) "Protein Annotation: Detective Work for Function Prediction", Trends in Genetics, 14(6):248-250.
Dubois et al. (Sep. 17, 1999) "Natural Splicing of Exon 2 of Human Interleukin-15 Receptor α-Chain mRNA Results in a Shortened Form with a Distinct Pattern of Expression", The Journal of Biological Chemistry, 274 (38):26978-26984.
Dubois et al. (2008) "Preassociation of IL-15 with IL-15Rα -IgG1-Fc Enhances Its Activity on Proliferation of NK and CD8 +/CD44high T Cells and Its Antitumor Action", Journal of Immunology, 180(4):2099-2106.
Dudley et al. (Sep. 2003) "Adoptive-cell-transfer therapy for the treatment of patients with cancer", Nature Review Cancer, 3:666-675.
Eisen et al. (1996) "Antigen-Specific T-Cell Receptors and Their Reactions with Complexes Formed by Peptides with Major Histocompatibility Complex Proteins", Advances in Protein Chemistry, 49:1-56.
Ellison et al. (Jul. 10, 1982) "The Nucleotide Sequence of a Human Immunoglobulin Cγ1 Gene", Nucleic Acids Research, 10(13):4071-4079.
Epardaud et al. (Apr. 15, 2008) "Interleukin-15/Interleukin-15Rα Complexes Promote Destruction of Established Tumors by Reviving Tumor-Resident CD8+ T Cells", Cancer Research, 68(8):2972-2983.
Fabbi et al. (2016) "Dual Roles of IL-15 in Cancer Biology", Journal of Cytokine Biology, 1(2):103, 7 pages.
Feldmann (May 1, 2002) "Development of Anti-TNF Therapy for Rheumatoid Arthritis", Nature Reviews Immunology volume, 2:364-371.
Felices et al. (Dec. 2016) "CD16-IL15-CD33 Trispecific Killer Engager (TriKE) Overcomes Cancer-Induced Immune Suppression and Induces Natural Killer Cell-Mediated Control of MDS and AML Via Enhanced Killing Kinetics", Blood, 128(22):4 pages.
Ferrari-Lacraz et al. (Dec. 15, 2006) "CD8+ T Cells Resistant to Costimulatory Blockade Are Controlled by an Antagonist Interleukin-15/Fc Protein", Transplantation, 82(11):1510-1517.
Ferrari-Lacraz et al. (Nov. 1, 2004) "Targeting IL-15 Receptor-Bearing Cells with an Antagonist Mutant IL-15/Fc Protein Prevents Disease Development and Progression in Murine Collagen-Induced Arthritis", The Journal of Immunology, 173(9):5818-5826.
Ferrarl-Lacraz et al. (Sep. 15, 2001) "An Antagonist IL-15/Fc Protein Prevents Costimulation Blockade-resistant Rejection", Journal of Immunology, 167(6):3478-3485.
Fleer (Oct. 1992) "Engineering Yeast for High Level Expression", Current Opinion in Biotechnology, 3 (5):486-496.
Frankel et al. (Oct. 2000) "Cell Surface Receptor-Targeted Therapy of Acute Myeloid Leukemia: A Review", Cancer Biotherapy & Radiopharmaceuticals, 15(5):459-476.
Gakamsky et al. (Sep. 2005) "CD8 Kinetically Promotes Ligand Binding to the T-Cell Antigen Receptor", Biophysical Journal, 89(3):2121-2133.
Garboczi et al. (Apr. 15, 1989) "HLA-A2-Peptide Complexes: Refolding and Crystallization of Molecules Expressed in *Escherichia coli* and Complexed with Single Antigenic Peptides", PNAS, 89(8):3429-3433.
Garboczi et al. (Nov. 14, 1996) "Structure of the Complex Between Human T-cell Receptor, Viral Peptide and HLA-A2", Nature, 384:134-141.
Gerber et al. (May/Jun. 2009) "Antibody Drug-conjugates Targeting the Tumor Vasculature—Current and Future Developments", mAbs, 1(3):247-253.
Gillies et al. (May 15, 2005) "An Anti-CD20-IL-2 Immunocytokine is Highly Efficacious in a SCID Mouse Model of Established Human B Lymphoma", Blood, 105(10):3972-3978.
Golay et al. (Nov. 14, 2013) "Glycoengineered CD20 Antibody Obinutuzumab Activates Neutrophils and Mediates Phagocytosis Through CD16B More Efficiently Than Rituximab", Blood, 122(20):3482-3491.

Gomes-Giacoia et al. (Jun. 2014) "Intravesical ALT-803 and BCG Treatment Reduces Tumor Burden in a Carcinogen Induced Bladder Cancer Rat Model; a Role for Cytokine Production and NK Cell Expansion", PLOS One, 9(6):11 Pages.
Graham et al. (Jul. 1977) "Characteristics of a Human Cell Line Transformed by DNA from Human Adenovirus Type 5", Journal of General Virology, 36(1):59-72.
Grunstein et al. (Oct. 1975) "Colony Hybridization: A Method for the Isolation of Cloned DNAs That Contain a Specific Gene", Proceedings of the National Academy of Sciences of the United States of America, 72(10):3961-3965.
Guglielmi et al. (Jul. 15, 2002) "Donor lymphocyte infusion for relapsed chronic myelogenous leuken1ia: prognostic relevance of the initial cell dose", Blood, 100(2):397-405.
Guo et al. (2013) "Therapeutic Cancer Vaccines: Past, Present and Future", Advances in Cancer Research, 119:421-475.
Han et al. (Oct. 22, 2011) "IL-15:IL-15 Receptor Alpha Superagonist Complex: High-Level Co-Expression in Recombinant Mammalian Cells, Purification and Characterization", Cytokine, 56(3):804-810.
Hara et al. (Nov. 1, 1995) "Implicating a Role for Immune Recognition of Self in Tumor Rejection: Passive Immunization Against the Brown Locus Protein", Journal of Experimental Medicine, 182(5):1609-1614.
Hatzimichael et al. (2010) "Hematopoietic Stem Cell Transplantation", Stem Cells and Cloning: Advances and Applications, 3:105-117.
Hayden-Ledbetter et al. (Apr. 2009) "CD20-Directed Small Modular Immunopharmaceutical, TRU-015, Depletes Normal and Malignant B Cells", Clinical Cancer Research, 15(8):2739-2746.
Hessell et al. (Sep. 6, 2007) "Fc Receptor but not Complement Binding is Important in Antibody Protection Against HIV", Nature, 449(7158):101-104.
Hezareh et al. (Dec. 2001) "Effector Function Activities of a Panel of Mutants of a Broadly Neutralizing Antibody against Human Immunodeficiency Virus Type 1", Journal of Virology, 75(24):12161-12168.
Hogquist et al. (Jan. 1994) "T Cell Receptor Antagonist Peptides Induce Positive Selection", Cell, 76(1):17-27.
Holliger et al. (Sep. 2005) "Engineered Antibody Fragments and the Rise of Single Domains", Nature Biotechnology, 23(9):1126-1136.
Hughes et al. (Apr. 2005) "Transfer of a TCR Gene Derived from a Patient with a marked Antitumor Response Conveys Highly Active T-Cell Effector Functions", Human Gene Therapy, 16(4):457-472.
Jakobisiak et al. (2011) "Interleukin 15 as a Promising Candidate for Tumor Imunotherapy", Cytokine & Growth Factor Reviews, 22:99-108.
Kaspar et al. (May 15, 2007) "The Antibody-mediated Targeted Delivery of Interleukin-15 and GM-CSF to the Tumor Neovasculature Inhibits Tumor Growth and Metastasis", Cancer Research, 67(10):4940-4948.
Kern et al. (Sep. 17, 1999) "Expression, Purification, and Functional Analysis of Murine Ectodomain Fragments of CD8αα and CD8αβ Dimers", The Journal of Biological Chemistry, 274:27237-27243.
Khantasup et al. (Dec. 1, 2015) "Design and Generation of Humanized Single-chain Fv Derived from Mouse Hybridoma for Potential Targeting Application", Monoclonal Antibodies in Immunodiagnosis and Immunotherapy, 34 (6):404-417.
Kim et al. (2012) "Humanization by CDR Grafting and Specificity-determining Residue Grafting", Methods in Molecular Biology, 907:237-245.
Kim et al. (Jul. 15, 1998) "Targeting the IL-15 Receptor with an Antagonist IL-15 Mutant/Fcγ2a Protein Blocks Delayed-Type Hypersensitivity", Journal of Immunology, 160(12):5742-5748.
Kimmel (1987) "Identification and Characterization of Specific Clones: Strategy for Confirming the Validity of Presumptive Clones", Methods in Enzymology, 152:507-511.
Klebanoff et al. (Feb. 17, 2004) "LI-15 Enhances the in Vivo Antitumor Activity of Tumor-Reactive Cos+ T Cells", Proceedings of the National Academy of Sciences of the United States of America, 101(7):1969-1974.

(56) References Cited

OTHER PUBLICATIONS

Kobayashi et al. (Dec. 15, 1994) "Tyrosinase Related Protein 1 (TRP1) Functions as a DHICA Oxidase in Melanin Biosynthesis", The EMBO Journal, 13(24):5818-5825.
Zheng et al. (Jan. 15, 2006) "An Antagonist Mutant IL-15/Fc Promotes Transplant Tolerance", Transplantation, 81(1):17 pages.
Zhu et al. Sep. 15, 2009, "Novel Human Interleukin-15 Agonists", Journal of Immunology, 183(6):3598-3607.
Zhu et al. (Mar. 1, 2006) "Visualization of p53(264-272)/HLA-A*0201 Complexes Naturally Presented on Tumor Cell Surface by a Multimeric Soluble Single-Chain T Cell Receptor", Journal of Immunology, 176(5):3223-3232.
(1988) Gene Characterization Kits, Stratagene Catalog, 2 pages.
International Preliminary Report on Patentability for Application No. PCT/US2008/005918, dated Nov. 17, 2009, 5 pages.
International Preliminary Report on Patentability for Application No. PCT/US2011/052545, dated Apr. 4, 2013, 12 pages.
International Preliminary Report on Patentability received for PCT International Application No. PCT/US16/53230, dated Apr. 5, 2018, 8 pages.
International Preliminary Report on Patentability received for PCT International Application No. PCT/US2015/038587, dated Jan. 12, 2017, 8 pages.
International Search Report and Written Opinion for PCT International Application no. PCT/US2011/052545, dated May 2, 2012, 16 pages.
International Search Report and Written Opinion for PCT International Application No. PCT/US2008/005918, dated Sep. 4, 2008, 6 pages.
International Search Report and Written Opinion received for PCT Patent International Application No. PCT/US2015/038587, dated Oct. 15, 2015, 9 pages.
International Search Report and Written Opinion received for PCT Patent International Application No. PCT/US2016/53230, dated Dec. 30, 2016, 11 pages.
Alam et al. (Feb. 1999) "Qualitative and Quantitative Differences in T Cell Receptor Binding of Agonist and Antagonist Ligands", Immunity, 10(2):227-237.
Alpdogan et al. (Jan. 2005) "IL-7 and IL-15: therapeutic cytokines for immunodeficiency", Trends in immunology, 25-26(1):56-64.
Anderson et al. (1995) "Functional Characterization of the Human Interleukin-15 Receptor αChain and Close Linkage of IL15RA and IL2RA Genes", The Journal of Biological Chemistry, 270(50):29862-29869.
Anonymous (May 15, 2014) "A Study of Intravesical BCG in Combination With ALT-803 in Patients with Non-Muscle Invasive Bladder Cancer", ClinicalTrials.gov, 9 Pages.
Arcaro et al. (Nov. 19, 2001) "CD8β Endows CD8 with Efficient Coreceptor Function by Coupling T Cell Receptor/CD3 to Raft-associated CD8/p56Ick Complexes", Journal of Experimental Medicine, 194(10):1485-1495.
Baeuerle et al. (Feb. 2009) "BiTE: Teaching Antibodies to Engage T-Cells for Cancer Therapy", Current Opinion in Molecular Therapeutics, 11(1):22-30.
Bailey et al. (Jul. 4, 2017) "New Interleukin-15 Superagonist (IL-15SA) Significantly Enhances Graft-versus-tumor Activity", Oncotarget, 8(27):44366-44378.
Bailey et al. (2013) "New Interleukin-15 Superagonist (IL-15 SA) Significantly Enhances Graft-Versus-Tumor Activity After Allogeneic Hematopoietic Stem Cell Transplantation", Blood, 122(21):05 pages.
Bazan et al. (Dec. 2012) "Phage display—A powerful technique for immunotherapy 1. Introduction and potential of therapeutic applications", Human Vaccines & Immunotherapeutics, 8(12):1817-1828.
Beers et al. (1999) "The Merck Manual of Diagnosis and Therapy", 17th Edition, 986-995.
Belmont et al. (Oct. 2006) "Potent Antitumor Activity of a Tumor-specific Soluble TCR/IL-2 Fusion Protein", Journal of Clinical Immunology, 121(1):29-39.
Benton et al. (Apr. 8, 1977) "Screening λgt Recombinant Clones by Hybridization to Single Plaques in Situ", Science, 196(4286):180-182.
Bergamaschi et al. (Feb. 15, 2008) "Intracellular Interaction of Interleukin-15 with its Receptor Alpha during Production Leads to Mutual Stabilization and Increased Bioactivity", Journal of Biological Chemistry, 283 (7):4189-4199.
Bernard et al. (Jun. 4, 2004) "Identification of an Interleukin-15α Receptor-binding Site on Human Interleukin-15", Journal of Biological Chemistry, 279(23):24313-24322.
Bessard et al. (Sep. 2009) "High Antitumor Activity of RLI, An Interleukin-15 (IL-15)-IL-15 Receptor α Fusion Protein, in Metastatic Melanoma and Colorectal Cancer", Molecular Cancer Therapeutics, 8(9):2736-2745.
Bevan (Aug. 1997) "In Thymic Selection, Peptide Diversity Gives and Takes Away", Immunity, 7(2):175-178.
Bjorkman (Apr. 18, 1997) "MHC Restriction in Three Dimensions: a View of T Cell Receptor/Ligand Interactions", Cell, 89(2):167-170.
Bork Peer (Apr. 2000) "Powers and Pitfalls in Sequence Analysis: The 70% Hurdle", Genome Research, 10(4):398-400.
Borras et al. (Mar. 19, 2010) "Generic Approach for the Generation of Stable Humanized Single-chain Fv Fragments from Rabbit Monoclonal Antibodies", The Journal of Biological Chemistry, 285(12): 9054-9066.
Bouchaud et al. (Sep. 26, 2008) "The Exon-3-Encoded Domain of IL-15Ralpha Contributes to IL-15 High-Affinity Binding and Is Crucial for the IL-15 Antagonistic Effect of Soluble IL-15Ralpha", Journal of Molecular Biology, 382(1):1-12.
Bruhns (2009) "Specificity and affinity of human Fγ receptors and their polymorphic variants for human IgG subclasses", Blood, 113(16):3716-3725.
Busch et al. (May 1, 2002) "Stabilization of Soluble, Low-Affinity HLA-DM/HLA-DR1 Complexes by Leucine Zippers", Journal of Immunological Methods, 263(1-2):111-121.
Cany et al. (Jan. 11, 2018) "Decitabine Enhances Targeting of AML Cells by CD34 + Progenitor-Derived NK Cells in NOD/SCID/IL2Rg null Mice", Blood, 131(2):202-214.
Capon et al. (Feb. 9, 1989) "Designing CD4 Immunoadhesins for AIDS Therapy", Nature, 337(6207):525-531.
Card et al. (Nov. 11, 2003) "A Soluble Single-Chain T-Cell Receptor IL-2 Fusion Protein Retains MHC-Restricted Peptide Specificity and IL-2 Bioactivity", Cancer Immunology, Immunotherapy, 53(4):345-357.
Chae et al. (1996) "Mutant IL-15 Protein exerting antagonistic effects on IL-15 triggered cell proliferation", Journal of the American Society of Nephrology, 7(9}:1654.
Chamow et al. (Feb. 1996) "Immunoadhesins: Principles and Applications", Trends Biotechnology, 14:52-60.
Chan et al. (May 2010) "Therapeutic Antibodies for Autoimmunity and Inflammation", Nature Reviews Immunology, 10(5):301-316.
Cheever (Apr. 2008) "Twelve Immunotherapy Drugs That Could Cure Cancers", Immunological Reviews, 222(1):357-368.
Chirifu et al. (Jul. 22, 2007) "Crystal Structure of the IL-15-IL-15Rα Complex, a Cytokine-Receptor Unit Presented in Trans", Nature Immunology, 8:1001-1007.
Chu et al. (Mar. 2016) "Therapeutic Effects of ALT-803, an IL-15 Superagonist, in Combination with Anti-CD20 Chimeric Antigen Receptor Modified Expanded Natural Killer Cells Against Burkitt Lymphoma (BL)", Biology of Blood and Marrow Transplantation, 22(3):1 page.
Cole et al. (Feb. 19, 2008) "T Cell Receptor Engagement of Peptide-Major Histocompatibility Complex Class I Does Not Modify CD8 Binding", Molecular Immunology, 45(9):2700-2709.
Conlon et al. (Jan. 1, 2005) "Redistribution, Hyperproliferation, Activation of Natural Killer Cells and CD8 T Cells, and Cytokine Production During First-In-Human Clinical Trial of Recombinant Human Interleukin-15 in Patients with Cancer", Journal of Clinical Oncology, 33(1):74-82.
Cragg et al. (Apr. 1, 2004) "Antibody Specificity Controls in Vivo Effector Mechanisms of Anti-Cd20 Reagents", Blood, 103(7):2738-2743.

(56) References Cited

OTHER PUBLICATIONS

Cuesta et al. (2009) "In Vivo Tumor Targeting and Imaging with Engineered Trivalent Antibody Fragments Containing Collagen-Derived Sequences", Plos One, e5381, 4(4):9 pages.

Daniels et al. (2000) "Critical Role for Cd8 in T Cell Receptor Binding and Activation by Peptide/Major Histocompatibility Complex Multimers", Journal of Experimental Medicine, 191(2):335-346.

Database Genbank (Sep. 21, 1994) "Human interleukin 15 (IL15) mRNA, complete cds", Genbank Accession No. U14407.1, 2 pages.

Database Genbank (Dec. 19, 1995) "Human interleukin-15 receptor alpha chain precursor (IL15RA) mRNA, complete cds", Genbank Accession No. U31628.1, 2 pages.

Database Genbank (Sep. 14, 1995) "'Mus Musculus Interleukin 15 (IL15) mRNA, complete cds", Genbank Accession No. U14332.1, 2 pages.

Database Genbank (May 20, 2005) "Mus Musculus Interleukin 15 Receptor, Alpha Chain, mRNA (cDNA clone Image:4457379), Complete cds", Genbank Accession No. BC095982.1, 2 pages.

Database UNIPROT (1999) "Sequence, retrieved from EBI, Database Accession No. 097687", XP002659759 (1999), 1 page.

Steel et al. (Feb. 1, 2010) "Interleukin-15 and its Receptor Augment Dendritic Cell Vaccination Against the neu Oncogene Through the Induction of Antibodies Partially Independent of CD4-help", Cancer Research, 70(3):1-19.

Stern et al. (Feb. 7, 1992) "The Human Class II MHC Protein HLA-DR1 Assembles as Empty Alpha Beta Heterodimers in the Absence of Antigenic Peptide", Cell, 68(3):465-477.

Stoklasek et al. (Nov. 1, 2006) "Combined IL-15/IL-15Rα Immunotherapy Maximizes IL-15 Activity in Vivo", Journal of Immunology, 177(9):6072-6080.

Sukumar et al. (2014) "Modulating Immunometabolism of Tumor Specific Mouse and Human Lymphocytes to Enhance T Cell Based Therapy for Cancer", Journal for ImmunoTherapy of Cancer, Article No. O2, 2(Suppl 3):2 pages.

Tai et al. (Sep. 15, 2010) "The Role of HER2 in Cancer Therapy and Targeted Drug Delivery", Journal of Controlled Release, 146(3):28 pages.

Tay et al. (2016) online published on Jul. 26, 2016, "TriKEs and BiKEs join CARs on the cancer immunotherapy highway", Human Vaccines & Immunotherapeutics, 12(11):2790-2796.

Terawaki et al. (Jul. 2007) "Specific and High-affinity Binding of Tetramerized PD-L1 Extracellular Domain to PD-1-expressing Cells: Possible Application to Enhance T Cell Function", International Immunology, 19(7):881-890.

Theobald et al. (Dec. 19, 1995) "Targeting P53 as a General Tumor Antigen", PNAS, 92(26)11993-11997.

Thomson et al. Aug. 1985) "Pigmentation-associated Glycoprotein of Human Melanomas and Melanocytes: Definition with a Mouse Monoclonal Antibody", Journal of Investigative Dermatology, 85(2):169-174.

Tietze et al. (Mar. 29, 2012) "Delineation of Antigen-Specific and Antigen-Nonspecific CD8(+) Memory T-Cell Responses after Cytokine-Based Cancer Immunotherapy", Blood, 119(13):3073-3083.

Tokuriki et al. (2009) "Stability effects of mutations and protein evolvability", Current Opinion in Structural Biology, 19:596-604.

Tomalia (1993) "Starburst/Cascade Dendrimers: Fundamental Building Blocks for a New Nanoscopic Chemistry Set", Aldrichimica Acta, 26(4):89-101.

Tonegawa (Apr. 14, 1983) "Somatic Generation of Immune Diversity", Bioscience Reports, 8(1):3-26.

Tough et al. (May 15, 2001) "An IFN-γ-Dependent Pathway Controls Stimulation of Memory Phenotype CD8+ T Cell Turnover in Vivo by IL-12, IL-18, and IFN-γ", Journal of Immunology, 166(10):6007-6011.

Traunecker et al., "Solubilizing the T-Cell Receptor-Problems in Solution", Immunology Today, 1989, 10(1):29-32.

Trevisani et al. (Jun. 2004) "Ethanol Causes Inflammation in the Airways by a Neurogenic and TRPV1-Dependent Mechanism", Journal of Pharmacology and Experimental Therapeutics, 309(3):1167-1173.

Trevisani et al. (2002) "Ethanol Elicits and Potentiates Nociceptor Responses via the Vanilloid Receptor-1", Nature Neuroscience, 5(6):546-551.

Tyagi et al. (Jan. 2004) "Urodynamic and Immunohistochemical Evaluation of Intravesical Capsaicin Delivery using Thermosensitive Hydrogel and Liposomes", The Journal of Urology, 171(1):483-489.

Urlaub et al. (Jul. 1980) "Isolation of Chinese Hamster Cell Mutants Deficient in Dihydrofolate Reductase Activity", Proceedings of the National Academy of Sciences, 77(7):4216-4220.

Valencia et al. (Mar. 15, 2013) "In Vitro Selection of Proteins with Desired Characteristics Using mRNA-display", Methods, 60(1):32 pages.

Valitutti (May 11, 1995) "Serial Triggering of Many T-Cell Receptors by a Few Peptide-MHC Complexes", Nature, 375(6527):148-151.

Van Den Bergh et al. (2015) "Interleukin-15: New Kid on the Block for Antitumor Combination Therapy", Cytokine and Growth Factor Reviews, 26:15-24.

Verbist et al. (Sep. 2012) "Function of IL-15 in Anti-Viral Immunity: Multiplicity and Variety", Cytokine, 59 (3):467-478.

Villinger et al. (Sep. 3, 2004) "IL-15 is Superior to IL-2 in the Generation of Long-Lived Antigen Specific Memory CD4 and CD8 T Cells in Rhesus Macaques", Vaccine, 22(25-26):3510-3521.

Vincent et al. (Oct. 2011) "CS14-6. Development of Two IL15 Immunocytokines Targeting Either GD2- or CD20-tumoral Bearing Cells", Cytokine, 56(1):1 Page.

Vincent et al. (Aug. 1, 2013) "Tumor Targeting of the IL-15 Superagonist RLI by an anti-GD2 Antibody Strongly Enhances Its Antitumor Potency", International Journal of Cancer, 133(3):757-765.

Wahl et al. (1987) "Molecular Hybridization of Immobilized Nucleic Acids: Theoretical Concepts and Practical Considerations", Methods in Enzymology, 152:399-407.

Waldmann et al. (2000) "IL-15 Receptors", 1521-1528.

Waldmann (Aug. 2006) "The Biology of Interleukin-2 and Interleukin-15: Implications for Cancer Therapy and Vaccine Design", Nature Reviews Immunology, 6(8):595-601.

Wang et al. (Aug. 15, 2009) "Structural Basis of the CD8αβ/MHC Class I Interaction: Focused Recognition Orients CD8β to a T Cell Proximal Position", The Journal of Immunology, 183(4):11 pages.

Ward et al. (Nov. 2009) "*Escherichia coli* Expression and Purification of Human and Cynomolgus IL-15", Protein Expression and Purification, 68(1):42-48.

Wei et al. (2001) "The Sushi Domain of Soluble IL-15 Receptor α Is Essential for Binding IL-15 and Inhibiting Inflammatory and Allogenic Responses In Vitro and In Vivo", The Journal of Immunology, 167:277-282.

Weidanz et al. (Dec. 1, 1996) "Display of Functional Alphabeta Single-Chain T-Cell Receptor Molecules on the Surface of Bacteriophage", Journal of Immunological Methods, 221(1-2):59-76.

Weiner (Sep. 2007) "Building Better Magic Bullets—Improving Unconjugated Monoclonal Antibody Therapy for Cancer", Nature Reviews Cancer, 7:701-706.

Wells (Sep. 18, 1990) "Additivity of Mutational Effects in Proteins", Biochemistry, 29(37):8509-8517.

Wen et al. (2008) "Targeting Activity of a TCR/IL-2 Fusion Protein Against Established Tumors", Cancer Immunology Immunother, 57(12):1781-1794.

Whitlow et al. (Apr. 1991) "Single-Chain Fv Proteins and their Fusion Proteins", Methods: A Companion to Methods in Enzymology, 2(2):97-105.

Wong et al. (May 1, 2012) "Efficacy and mechanism-of-action of a novel superagonist IL-15:IL-15Rα/Fc fusion complex in murine multiple myeloma syngeneic mouse models (46.44)", The Journal of Immunology, 188(Suppl 1):04 pages.

Wong et al. (2011) "Interleukin-15:Interleukin-15 Receptor α Scaffold for Creation of Multivalent Targeted Immune Molecules", Protein Engineering, Design & Selection, 24(4):373-383.

(56) References Cited

OTHER PUBLICATIONS

Wong et al. (Nov. 2013) "The IL-15-based superagonist ALT-803 promotes the antigen-independent conversion of memory CD8+ T cells into innate-like effector cells with antitumor activity", Oncoimmunology, Article No. e26442, 2 (11):3 pages.
Wooldridge et al. (Jul. 29, 2005) "Interaction between the CD8 Coreceptor and Major Histocompatibility Complex Class I Stabilizes T Cell Receptor-Antigen Complexes at the Cell Surface", The Journal of Biological Chemistry, 280:27491-27501.
Wu Jennifer, (Oct. 28, 2013) "IL-15 Agonists: The Cancer Cure Cytokine", Journal of Molecular and Genetic Medicine, 7(4):3 pages.
Xu et al. (May 15, 2013) "Efficacy and Mechanism-of-Action of a Novel Superagonist Interleukin-15: Interleukin-15 Receptor αSu/Fc Fusion Complex in Syngeneic Murine Models of Multiple Myeloma", Therapeutics, Targets and Chemical Biology, 73(10):3075-3086.
Xuan et al. (Apr. 8, 2010) "Targeted Delivery of Interferon-Alpha via Fusion to Anti-CD20 Results in Potent Antitumor Activity against B-Cell Lymphoma", Blood, 115(14):2864-2871.
Yang et al. (2008) "Clinical-Scale Lentiviral Vector Transduction of PBL for TCR Gene Therapy and Potential for Expression in Less Differentiated Cells", Journal of Immunotherapy, 31(9):15 pages.
Yu et al. (Apr. 17, 2012) "Simultaneous Inhibition of Two Regulatory T-Cell Subsets Enhanced Interleukin-15 Efficacy in a Prostate Tumor Model", Proceedings of the National Academy of Sciences of the United States of America, 109 (16):6187-6192.
Zah et al. (Jun. 2016) "T Cells Expressing CD19/CD20 Bispecific Chimeric Antigen Receptors Prevent Antigen Escape by Malignant B Cells", Cancer Immunology Research, 4(6):498-508.
Zhang et al. (May 5, 2009) "Interleukin-15 Combined with an Anti-CD40 Antibody Provides Enhanced Therapeutic Efficacy for Murine Models of Colon Cancer", Proceedings of the National Academy of Sciences of the United States of America, 106(18):7513-7518.
Zhang et al. (May 1998) "Potent and Selective Stimulation of Memory-Phenotype CD8+ T Cells in Vivo by IL-15", Immunity, 8(5):591-599.
Zhao et al. (Nov. 1, 2007) "High-Affinity TCRs Generated by Phage Display Provide CD4+ T Cells with the Ability to Recognize and Kill Tumor Cell Lines", The Journal of Immunology, 179(9):5845-5854.
Kostelny et al. (Mar. 1, 1992) "Formation of a Bispecific Antibody by the Use of Leucine Zippers", Journal of Immunology, 148(5):1547-1553.
Kouzarides et al. (Aug. 17, 1989) "Leucine Zippers of Fos, Jun and GCN4 Dictate Dimerization Specificity and Thereby Control DNA Binding", Nature, 340:568-571.
Kouzarides et al. (Dec. 15, 1988) "The Role of the Leucine Zipper in the Fos-jun Interaction", Nature, 336:646-651.
Kruif et al. (Mar. 29, 1996) "Leucine Zipper Dimerized Bivalent and Bispecific scFv Antibodies from a Semisynthetic Antibody Phage Display Library", The Journal of Biological Chemistry, 271:7630-7634.
Kubetzko et al. (Nov. 17, 2006) "PEGylation and Multimerization of the Anti-p185HER-2 Single Chain Fv Fragment 4D5 Effects on Tumor Targeting", The Journal of Biological Chemistry, 281:35186-35201.
Laugel et al. (Aug. 17, 2007) "Different T Cell Receptor Affinity Thresholds and CD8 Coreceptor Dependence Govern Cytotoxic T Lymphocyte Activation and Tetramer Binding Properties", The Journal of Biological Chemistry, 282:23799-23810.
Lawrencia et al. (May 2001) "Transfection of Urothelial Cells using Methyl-β-Cyclodextrin Solubilized Cholesterol and Dotap", Gene Therapy, 8(10):760-768.
Lazar et al. (Mar. 14, 2006) "Engineered Antibody Fc Variants with Enhanced Effector Function", Proceedings of the National Academy of Sciences, 103(11): 4005-4010.
Lazar et al. (Mar. 1988) "Transforming Growth Factor Alpha: Mutation of Aspartic Acid 47 and Leucine 48 Results in Different Biological Activities", Molecular and Cellular Biology, 8(3):1247-1252.
Lin et al. (Aug. 10, 1990) "Expression of T Cell Antigen Receptor Heterodimers in a Lipid-Linked Form", Science, 249(4969):677-679.
Liu et al. (Dec. 2014) "Evaluation of a Novel CD2O-Targeted IL-15 Immunotherapeutic with Potent Activity Against B Cell Lymphoma", Journal for ImmunoTherapy of Cancer, 2(Suppl 3):1 page.
Lu et al. (2009) "Construction and Production of an IgG-like Tetravalent Bispecific Antibody for Enhanced Therapeutic Efficacy", Methods in Molecular Biology, 525:377-404.
Matsumoto et al. (Nov. 2011) "Intravesical Interleukin-15 Gene Therapy in an Orthotopic Bladder Cancer Model", Human Gene Therapy, 22(11):1423-1432.
McLaughlin et al. (2015) "Adoptive T-cell therapies for refractory/relapsed leukemia and lymphoma: current strategies and recent advances", Therapy Advance Hematology, 6(6):295-307.
Mohler et al. (Aug. 1, 1993) "Soluble Tumor Necrosis Factor (TNF) Receptors are Effective Therapeutic Agents in Lethal Endotoxemia and Function Simultaneously as Both TNF Carriers and TNF Antagonists", The Journal of Immunology, 151(3):1548-1561.
Mortier et al. (Jan. 20, 2006) "Soluble Interleukin-15 Receptor α (IL-15Rα)-sushi as a Selective and Potent Agonist of IL-15 Action through IL-15Rβ/γ", The Journal of Biological Chemistry, 281(3):1612-1619.
Moskaug et al. (Sep. 15, 1989) "Translocation of Diphtheria Toxin A-Fragment to the Cytosol. Role of the Site of Interfragment Cleavage", Journal of Biological Chemistry, 264(26):15709-15713.
Mosquera et al. (Apr. 1, 2005) "In Vitro and In Vivo Characterization of a Novel Antibody-Like Single-Chain TCR Human IgG1 Fusion Protein", Journal of Immunology, 174(7):4381-4388.
Neveu et al. (Jul. 2006) "Impact of CD8—MHC Class I Interaction in Detection and Sorting Efficiencies of Antigen-Specific T Cells Using MHC Class I/peptide Multimers: Contribution of pMHC Valency", International Immunology, 18 (7):1139-1145.
Ng et al. (2005) "Liposomal Polyene Antibiotics", Methods in Enzymology, 391:304-313.
Nogawa et al. (Apr. 2005) "Intravesical Administration of Small Interfering RNA Targeting PLK-1 Successfully Prevents the Growth of Bladder Cancer", Journal of Clinical Investigation, 115(4):978-985.
Novellino et al. (Mar. 2005) "A Listing of Human Tumor Antigens Recognized by T Cells: Mar. 2004 Update", Cancer Immunology, Immunotherapy, 54(3):187-207.
Nugent et al. (May 15, 2005) "Low Binding Capacity of Murine Tetramers Mutated at Residue 227 Does Not Preclude the Ability to Efficiently Activate CD8+ T Lymphocytes", Immunology Letters, 98(2):208-215.
Oleksiewicz et al. (Jun. 13, 2012) "Anti-bacterial Monoclonal Antibodies: Back to the Future?", Archives of Biochemistry and Biophysics, 526(2):124-131.
Olsnes et al. (1982) "Chimeric Toxins", Pharmacology and Therapeutics, 15(3):355-381.
Orti et al. (2017) "Donor lymphocyte infusions in AML and MDS: Enhancing the graft-versus-leuke1nia effect", Experimental Hematology, 48:1-11.
Ortiz-Sánchez et al. (May 2008) "Antibody-cytokine Fusion Proteins: Applications in Cancer Therapy", Expert Opinion on Biological Therapy, 8(5):609-632.
Otegbeye et al. (Dec. 3, 2015) "The IL-15 Super-Agonist ALT-803 Promotes Superior Activation and Cytotoxicity of Ex Vivo Expanded NK Cells Against AML", Blood, 3090, 126(23):4 Pages.
Parmiani et al. (Feb. 15, 2007) "Unique Human Tumor Antigens: Immunobiology and Use in Clinical Trials", The Journal of Immunology, 178(4):1975-1979.
Pastan et al. (Dec. 5, 1986) "Immunotoxins", Cell, 47:641-648.
Pastan et al. (1992) "Recombinant Toxins as Novel Therapeutic Agents", Annual Review Biochemistry, 61:331-354.
Penichet et al. (1997) "Antibody-IL-2 Fusion Proteins: A Novel Strategy for Immune Protection", Human Antibodies, 8(3):106-118.

(56) References Cited

OTHER PUBLICATIONS

Pettit et al. (Jan. 24, 1997) "Structure-Function Studies of Interleukin 15 Using Site-Specific Mutagenesis, Polyethylene Glycol Conjugation, and Homology Modeling", Journal of Biological Chemistry, 272(4):2312-2318.

Quemener et al. (Nov. 15, 2006) "Docking of Human interleukin-15 to Its Specific Receptor Alpha Chain: Correlation Between Molecular Modeling and Mutagenesis Experimental Data", Proteins, 65(3):623-636.

Rabinowitz et al. (Feb. 20, 1996) "Kinetic Discrimination in T-cell Activation", Proceedings of the National Academy of Sciences of the United States of America, 93(4):1401-1405.

Ramos et al. (Apr. 10, 2015) "Current Approaches in the Treatment of Relapsed and Refractory Acute Myeloid Leukemia", Journal of Clinical Medicine, 4(4):665-695.

Richards et al. (Aug. 2008) "Optimization of Antibody Binding to FcγRIIa Enhances Macrophage Phagocytosis of Tumor Cells", Molecular Cancer Therapeutics, 7(8):2517-2527.

Rieker et al. (2000) "Molecular Applications of Fusions to Leucine Zippers", Methods in Enzymology, 328:282-296.

Rossi et al. (Oct. 29, 2009) "CD2O-Targeted Tetrameric Interferon-α, A Novel and Potent Immunocytokine for the Therapy of B-Cell Lymphomas", Blood, 114(18):3864-3871.

Roychowdhury et al. (Nov. 1, 2004) "Failed 1-15 Adoptive Immunotherapy with Tumor-Specific T Cells: Reversal with Low-Dose Interleukin 15 but not Low-Dose Interleukin 2", Cancer Research, 64(21):8062-8067.

Rubenstein et al. (Jun. 13, 2006) "Converting IL-15 to a Superagonist by Binding to Soluble IL-15Rα", Proceedings of the National Academy of Sciences of the United States of America, 103(24):9166-9171.

Sauter et al. (Apr. 29, 2013) "Interleukin-15 Administration Increases Graft-Versus-Tumor Activity in Recipients of Haploidentical Hematopoietic SCT", Bone Marrow Transplantation, 48(9):1237-1242.

Savio et al. (Apr. 2006) "IL-15: A Relevant Cytokine for Lymphoid Homeostasis and Autoimmune Diseases", Biotecnologia Aplicada, 23(2):7 pages.

Schmohl et al. (Jul. 2016) "Enhanced ADCC and NK Cell Activation of an Anticarcinoma Bispecific Antibody by Genetic Insertion of a Modified IL-15 Cross-linker", TriKE Facilitates ADCC and Sustaining of NK Cells, Molecular Therapy, 24(7):1312-1322.

Schott et al. (Dec. 2002) "Mouse MHC Class I Tetramers That Are Unable to Bind to CD8 Reveal the Need for CD8 Engagement in Order to Activate Naive CD8 T Cells", European Journal of Immunology, 32(12):3425-3434.

Shen et al. (Apr. 21, 2006) "Single Variable Domain-IgG Fusion a Novel Recombinant Approach to Fc Domain-Containing Bispecific Antibodies", The Journal of Biological Chemistry, 281:10706-10714.

Skolnick et al. (2000) "From Genes to Protein Structure and Function: Novel Applications of Computational Approaches in the Genomic Era", Trends in Biotechnology, 18(1):34-39.

Sliwkowski et al. (Sep. 13, 2013) "Antibody Therapeutics in Cancer", Science, 341(6151):1192-1198.

Sloan et al. (Jun. 29, 1995) "Mediation by HLA-DM of Dissociation of Peptides from HLA-DR", Nature, 375:802-806.

Sprent et al. (Mar. 29, 2000) "T-cell Proliferation in Vivo and the Role of Cytokines", Philosophical Transactions of the Royal Society of London, Series B, Biological Sciences, 355(1395):317-322.

Gomes et al. (May 5, 2013) "IL-15 Analogue (ALT-603) Targeting T Regulatory Cells Causes Tumor Burden Reduction in an Orthotopic Non-Muscle Invasive Bladder Cancer Model", The Journal of Urology, 189(4S):e238-e239.

Vincent et al. (Nov. 2013) "Antitumor Activity of an Immunocytokine Composed of an Anti-GD2 Antibody and the IL-15 Superagonist RLI", OncoImmunology, e26441, 2(11):3 pages.

SUPERKINE

This application is a continuation-in-part of 1) International Application PCT/US2017/066449 (WO2018/112219) having an International filing date of Dec. 14, 2017, which claims priority to U.S. provisional application with Ser. No. 62/434,389, filed on Dec. 14, 2016 and 2) U.S. patent application Ser. No. 15/951,042, filed Apr. 11, 2018 which is a continuation of U.S. patent application Ser. No. 15/083, 998, filed Mar. 29, 2016 which is a continuation of U.S. patent application Ser. No. 13/854,903, filed Apr. 1, 2013, which is a continuation of U.S. patent application Ser. No. 13/769,179, filed Feb. 15, 2013, which is a continuation-in-part of U.S. patent application Ser. No. 13/238,925, filed Sep. 21, 2011, which claims the benefit of U.S. Provisional Patent Application Ser. No. 61/527,911, filed Aug. 26, 2011 and claims the benefit of U.S. Provisional Patent Application No. 61/384,817, filed Sep. 21, 2010. U.S. patent application Ser. No. 13/854,903, filed Apr. 1, 2013, is also a continuation-in-part of said U.S. patent application Ser. No. 13/238, 925. The entire contents of these applications are incorporated herein by reference in their entirety.

FIELD OF THE INVENTION

The field of the invention is cancer therapy, especially as it relates to cancer therapy with multifunctional chimeric molecule complexes.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Most commonly, treatment for patients diagnosed with acute lymphoblastic leukemia (ALL) includes induction, consolidation, and maintenance therapy along with CNS prophylaxis. For example, induction therapy is often based on a combinations of various drugs, including vincristine, prednisone, cyclophosphamide, doxorubicin, and L-asparaginase, over about 4-6 weeks, which is followed by consolidation. In many cases, consolidation includes administration of multiple drugs, including cytarabine and methotrexate. Maintenance therapy often includes 6-mercaptopurine, methotrexate, steroids, and vincristine (while intrathecal methotrexate may be administered throughout).

More recently, intensive multi-agent chemotherapy (see e.g., the CALGB [Cancer and Leukemia Group B]-8811 and hyper-CVAD [hyperfractionated cyclophosphamide, vincristine, doxorubicin, and dexamethasone] regimens and the ALL-2 regimen) plus the administration of tyrosine kinase inhibitors for Philadelphia chromosome—positive ALL and rituximab for CD20-positive ALL has resulted in 3-y survivals of 50% or more in adults. Unfortunately, as will be readily appreciated, use of multiple drugs often precipitate undesirable side effects and so add a significant burden to the wellbeing of the patient. Some leukemia patients may require a hematopoietic stem cell transplant to fully eradicate the diseased cells. In this procedure, high-dose chemotherapy, with or without radiation, is first used to ablate the patient's bone marrow. Then bone marrow stem cells from an immunologically matched donor (or from the patient's own body) are given back to the patient. The transplanted stem cells then grow and repopulate the bone marrow and blood with healthy cells. However, such procedure is relatively risky and may not be an option for all patients.

In other known treatment methods, acute lymphoblastic leukemia (ALL) is treated using immune therapy. For example, CAR-T cell therapy targeting CD19 has shown remarkable efficacy in some patients, however, antigen escape of other malignant cells have not afforded complete and durable remission. To overcome such disadvantages, single chain bi-specific scfVs were employed in a CAR for adoptive T cell transfer (see e.g., Cancer Immunol Res. 2016 June; 4(6): 498-508). However, modified T cells are often very difficult to prepare in therapeutic quantities. In addition, the bi-specific CAR may elicit an immune response and as such not achieve full therapeutic effect.

In still further known treatments, certain chimeric molecules have been prepared in which two scFv portions were fused to provide a bi-specific therapeutic agent. For example, one bispecific therapeutic agent had single-chain variable fragments (scFv) against CD16 on NK cells and against EpCAM on tumor cells to so facilitate ADCC (antigen-specific antibody dependent cell-mediated cytotoxicity. To improve on the ADCC of such therapeutics, the two scFv portions were coupled together via an IL15 portion to form a multi-component chimeric protein (TriKE, tri-specific killer engager; see e.g., Molecular Therapy Vol. 24 No. 7 Jul. 2016, 1312-1322; Human Vaccines & Immunotherapeutics 2016, vol. 12, No. 11, 2790-2796;Blood 2016 128: 4291). Other treatments used a multimeric IL-15 based molecule that included a CD3 binding domain as is described in WO 2017/205726.

While such therapeutics improve the efficacy of treatment and also stimulate NK cells, they may deplete a patient's immune system of healthy cells (T cells) where such cells express a marker that is targeted by the therapeutic (CD3). For example, most T cells express CD3 and as such will be subject to NK attack or complement dependent cytotoxicity where the therapeutic agent targets CD3. Similarly, immature B cells express among other markers CD19 and CD20, and will therefore also be attacked by T cells where the therapeutic agent comprises an anti-CD3 and an anti-CD19 portion. Moreover, ALL cell populations are also often genetically heterogeneous and will include cells that do not express CD19, or CD20.

Thus, even though there are numerous therapeutic agents known in the art, all or almost all of them suffer from various disadvantages. Therefore, there remains a need for improved compositions and methods to treat ALL using immune therapy.

SUMMARY OF THE INVENTION

The inventor has now discovered compositions and methods in which multifunctional chimeric molecule complexes are used for the treatment of acute lymphoblastic leukemia. In especially preferred aspects, contemplated multifunctional chimeric molecule complexes will stimulate an immune response to cancerous cells via an IL15/IL15Rα portion (e.g., via NK cell cytotoxicity and complement dependent cytotoxicity) and target a diverse population of ALL cells via more than one marker of diseased cells. In further preferred aspects, it is also contemplated that the compositions and methods will not target CD3 and as such will not trigger off-target cytotoxicity.

In one aspect of the inventive subject matter, the chimeric molecule complex includes a first fusion protein comprising an Fc portion, an IL15 receptor portion, and a first affinity portion, wherein the first affinity portion specifically binds to one of CD19, CD20, and CD22. Contemplated chimeric molecule complexes will further include a second fusion protein comprising an IL15 portion and a second affinity portion, wherein the second affinity portion specifically binds to one of CD19, CD20, and CD22. Most typically, the first and second fusion proteins form a complex via the IL15 portion and the IL15 receptor portion.

For example, preferred molecule complexes include first and second affinity portions that bind different ones of CD19, CD20, and CD22, and/or at least one of the first affinity portion and the second affinity portion comprise an scFv. Particularly preferred IL15 portion comprise an IL15 N72D mutant and preferred IL15 receptor portions comprise IL15Rα. While fusion proteins may advantageously be prepared as recombinant polypetides in which a single polypeptide chain includes all portions, it is also contemplated that the IL15 receptor portion and the first affinity portion and/or the IL15 portion and the second affinity portion are coupled to each other via a binding portion (e.g., at least a portion of biotin, Protein A, Protein B, and/or an RNA fragment). Where desired, at least one of the first and second fusion proteins may also comprise an affinity portion that binds to CD3. Most typically, the Fc portion of the first fusion protein will comprise at least a portion of an IgG, IgM, IgA, IgD, and/or IgE antibody.

In further preferred examples, contemplated molecule complexes will form at least a dimer with at least a second chimeric molecule complex. Most typically, the second chimeric molecule complex will comprise a third fusion protein comprising an Fc portion, an IL15 receptor portion, and a third affinity portion, wherein the third affinity portion specifically binds to one of CD19, CD20, and CD22; and a fourth fusion protein comprising an IL15 portion and a fourth affinity portion, wherein the fourth affinity portion specifically binds to one of CD19, CD20, and CD22. Preferably, the third and fourth fusion proteins form a complex via the IL15 portion and the IL15 receptor portion.

Furthermore, it is contemplated that the third and the fourth affinity portions bind different ones of CD19, CD20, and CD22. For example, at least one of the third and the fourth affinity portions bind to different ones of CD19, CD20, and CD22 with respect to the first and the second affinity portions. Optionally, one of the first, second, third, and fourth affinity portions may also bind to CD3 instead of to one of CD19, CD20, and CD22.

Most typically, at least one of the first, second, third, and fourth affinity portion comprise an scFv, and the IL15 receptor portion and the first affinity portion and/or the IL15 portion and the second affinity portion form a single polypeptide. Additionally, in at least some aspects of the inventive subject matter, at least one Fc portion of the first and third fusion protein is coupled to an albumin. In still further contemplated aspects, at least one of the affinity portions may also be a BiKE or TriKE.

Preferably, at least one of the affinity portions comprises a scFv portion with CDR regions grafted from or otherwise obtained from a therapeutic antibody against one of CD19, CD20, and CD22, and typical therapeutic antibody examples include blinatumomab, denintuzumab, rituximab, taplitumomab, afutuzumab, ofatumumab, obinutuzumab, lymphomun, ibritumomab, ocrelizumab, ocaratuzumab, ublituximab, veltuzumab, bectumomab, epratuzumab, inotuzumab, moxetumomab, and pinatuzumab.

In further aspects of the inventive subject matter, the inventor also contemplates recombinant nucleic acids comprising a sequence segment encoding at least one of the first and second fusion proteins contemplated herein, as well as recombinant cells that comprising such recombinant nucleic (as extrachromosomal units or integrated in to the genome of the host cell). Still further contemplated aspects include pharmaceutical compositions for treatment of acute lymphocytic leukemia that will comprise a pharmaceutically acceptable carrier in combination with a chimeric molecule complex as presented herein. Thus, use of contemplated chimeric molecule complexes to treat acute lymphocytic leukemia is also contemplated. Consequently, the inventor contemplates a method of treating acute lymphocytic leukemia that comprises a step of administering a chimeric molecule complex as contemplated herein to a patient in need thereof under a protocol effective to reduce leukemia cells in the patient.

Various objects, features, aspects and advantages of the inventive subject matter will become more apparent from the following detailed description of preferred embodiments, along with the accompanying drawing.

DETAILED DESCRIPTION

The inventive subject matter is directed to compositions and methods that provide, in the context of treatment of acute lymphoblastic leukemia, a chimeric molecule complex with multiple desirable functions for (1) targeting cancer cells, (2) activating an immune response; and (3) enabling persistence of the chimeric molecule complex to ensure the proper response. Advantageously, by selection of appropriate affinity portions, ALL cells can be selectively targeted and eliminated with no off-target specificity, for example, towards immature T cells expressing CD3. Cytotoxic effect is nevertheless maintained by inclusion of an IL15/IL15 receptor portion that activates NK cells and by inclusion of an Fc portion of an antibody that helps direct complement dependent cytotoxicity towards ALL cells. The inventors have thus discovered that by generating a chimeric molecule complex with multiple key functions, the therapeutic efficacy can be greatly increased while avoiding undesirable T cell depletion.

Figure 1:
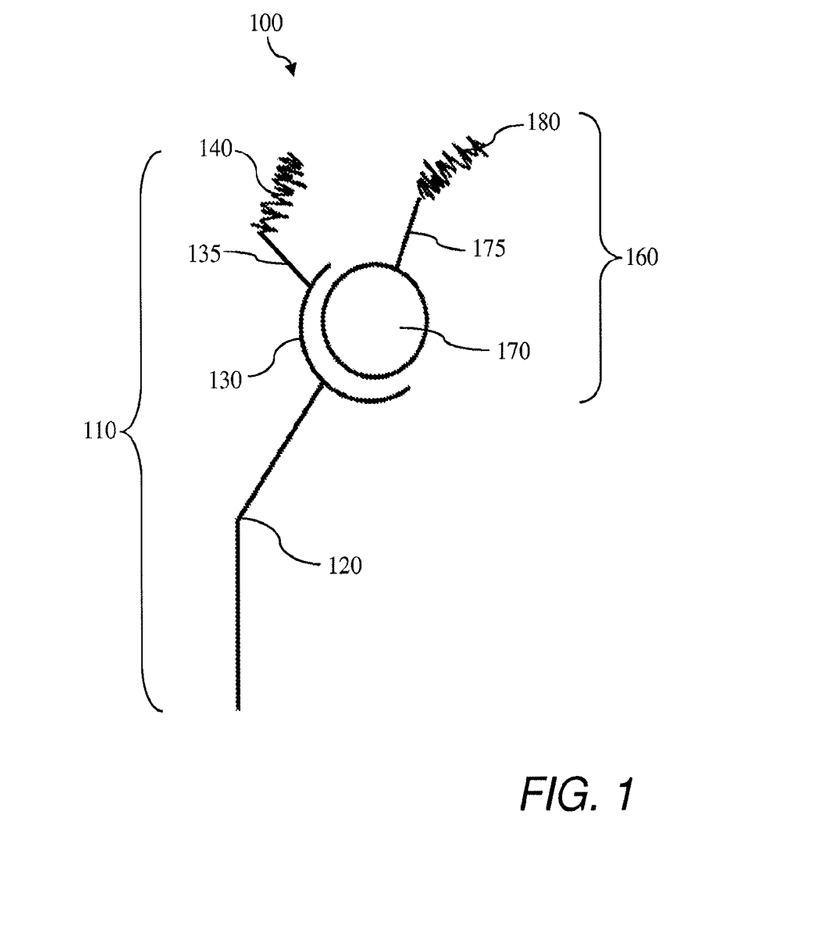
FIG. 1 illustrates an exemplary chimeric molecule complex.

FIG. 1 schematically illustrates one exemplary embodiment of a chimeric molecule complex 100. Chimeric molecule complex 100 comprises first fusion protein 110 and second fusion protein 160. The first fusion protein 110 has Fc portion 120, IL15 receptor portion 130, and a first affinity portion 140. The IL15 receptor portion is preferably an IL15 receptor alpha chain. First affinity portion 140 is coupled to IL15 receptor portion 130 via first linker 135. Second fusion protein 160 has IL15 portion 170 coupled to second affinity portion 180 via second linker 175. It should be noted that as used herein, the term "IL15 portion" also expressly includes its mutant forms, and particularly IL15N72D. Thus, the IL15 portion may be a native (typically human) IL15 or an IL15 superagonist. In preferred embodiments, first and second fusion proteins 110 and 160 form a complex via non-covalent but specific binding of the IL15 portion 170 to the IL15 receptor portion 130.

It should be appreciated that chimeric molecule complexes can be combined in dimers (or higher multimers, depending on the type of Fc portion selected), which can increase not only the effectiveness but also the number of functions of treatment. It should also be noted that such dimers need not necessarily comprise identical chimeric molecule complexes, but may indeed comprise distinct chimeric molecule complexes that so allow additional targeting (e.g., the first chimeric molecule complex targets CD19 and CD20, while the second chimeric molecule complex targets CD22 and CD20).

Figure 2:
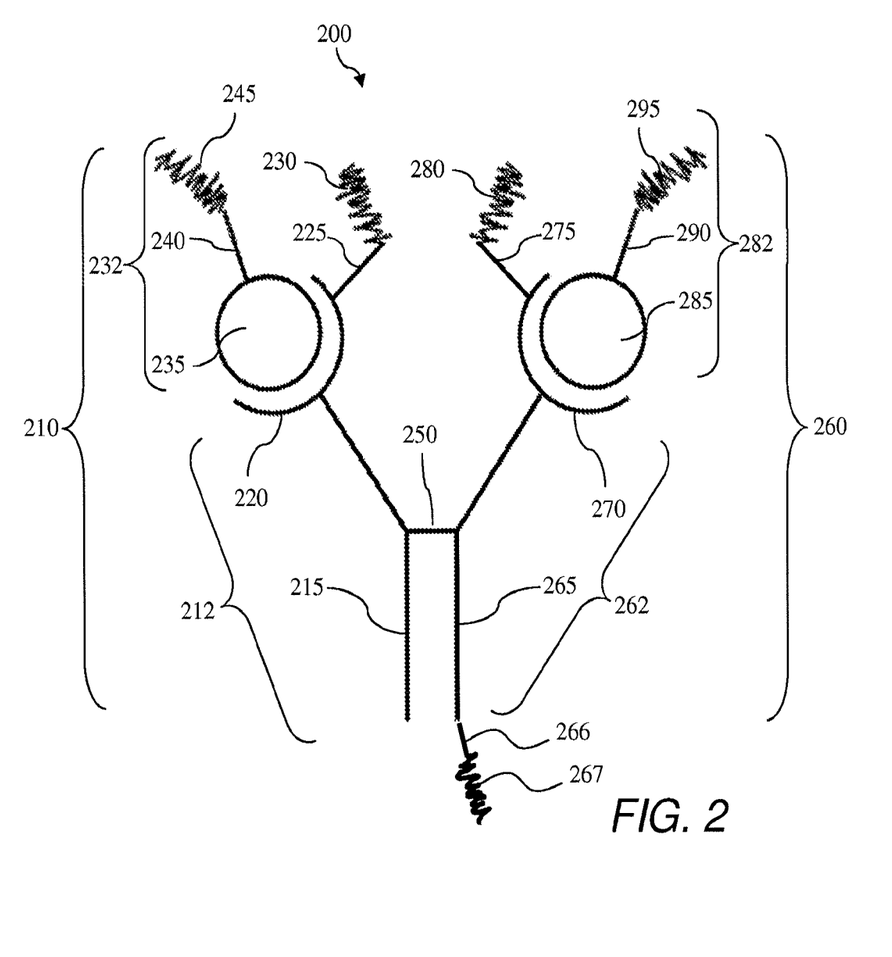
FIG. 2 illustrates an exemplary dimer formed of two chimeric molecule complexes.

FIG. 2 schematically and exemplarily illustrates one embodiment of a dimer 200 formed of first chimeric molecule complex 210 and second chimeric molecule complex 260. First chimeric molecule complex 210 comprises first fusion protein 212 and second fusion protein 232. The first fusion protein has an Fc portion 215, IL15 receptor portion 220, and a first affinity portion 230. The IL15 receptor portion is preferably a (human) IL15 receptor alpha chain. First affinity portion 230 is coupled to IL15 receptor portion 220 via first linker 225. Second fusion protein 232 has a (human) IL15 portion 235 coupled to second affinity portion 245 via second linker 240.

Similarly, second chimeric molecule complex 260 comprises third fusion protein 262 and fourth fusion protein 282. The third fusion protein has Fc portion 265, IL15 receptor portion 270, and a third affinity portion 280, coupled to IL15 receptor portion 270 via third linker 275. The IL15 receptor portion is preferably a (human) IL15 receptor alpha chain. Fourth fusion protein 282 has a (human) IL15 portion 285 coupled to fourth affinity portion 295 via fourth linker 290. Where desired, a fifth affinity portion 267 may be coupled to the Fc portion 265 of the third fusion protein 262 via fifth linker 266. Of course, it should be appreciated that the fifth affinity portion may also be coupled to the Fc portion 215 or to any one of first through fourth affinity portions, not illustrated. In the example of FIG. 2, the first chimeric molecule complex 210 and the second chimeric molecule complex 260 are bound together via disulfide bond 250 (and hydrophobic interactions between Fc portions). As noted above, it should be appreciated that in at least some embodiments dimer 200 is a heterodimer, where first chimeric molecule complex 210 and second chimeric molecule complex 260 are different, most typically by virtue of different affinity portions. Therefore, multiple advantageous functions can be combined in one dimer.

In order to facilitate the precise targeting of ALL cancer cells, it is contemplated that chimeric molecule complex 100 contains affinity portions, such as first affinity portion 140 and second affinity portion 180, which will preferably bind with cancer-specific antigens. In ALL, for example, it is contemplated that the diseased cells present surface proteins CD19, CD20, and CD22. Notably, as ALL cells are often heterogeneous in population, a fraction of ALL cells may not express CD19, CD20, and/or CD22. Consequently, therapies targeting only one of the surface markers will likely not eradicate cancer cells lacking that surface marker. Therefore, in some preferred embodiments, first affinity portion 140 and/or second affinity portion 180 will have an affinity toward at least a portion of one or more, and most typically at least two or more of CD19, CD20, and CD22. Where desired, one of the affinity portions may also have affinity towards CD3, a T cell specific marker to so attract and bind a cytotoxic T cell to the ALL B cell. For example, in some preferred embodiments, first affinity portion 140 comprises an antibody fragment, most typically a scFv, which binds to the target molecule. However, it is also contemplated that first affinity portion 140 and/or second affinity portion 180 may also comprise an aptamer, a protein identified by phage or mRNA display, or other CD19, CD20, CD22, or CD3, or specific ligands that target and bind to CD19, CD20, CD22, or CD3, respectively.

In some circumstances it may be desirable for first affinity portion 140 to have an affinity to a molecule distinct from the affinity of second affinity portion 180. This would allow for more refined targeting of multiple targets on the ALL cells. While not wishing to limit the subject matter, it is contemplated, for example, first affinity portion 140 could have an affinity to CD19 and second affinity portion 180 could have an affinity to CD20 or CD22 (or CD3 where T cell targeting is desired). Or, first affinity portion 140 could have an affinity to CD20 and second affinity portion 180 could have an affinity to CD19, CD22, or CD3. Further still, first affinity portion 140 could have an affinity to CD22 and second affinity portion 180 could have an affinity to CD19, CD20, or CD3. Finally, in yet another example, first affinity portion 140 could have an affinity to CD3 and second affinity portion 180 could have affinity to CD19, CD20, or CD22. Of course, where contemplated chimeric molecule complexes form a dimer (or higher multimer), a first chimeric molecule complex may have identical affinity portions (e.g., first and second affinity portions binding CD19, or CD20, or CD22) while the second chimeric molecule complex may have identical or different affinity portions as discussed above. It should be appreciated that the affinity portions may have other targets besides Cluster of Differentiation (CD) molecules, such as various cancer-specific antigens or tumor neoepitopes.

Regardless of the particular arrangement, it should be appreciated that the so formed chimeric molecule complexes will allow for specific binding not only to a genetically diverse population of ALL cells collectively expressing one or more of CD19, CD20, and CD22, but that such chimeric molecule complexes will also lead to crosslinking ALL cells via the first through fourth (and higher) affinity portions. Notably, contemplated compositions need not bind to CD3 of cytotoxic T cells to so exert therapeutic effect, but will nevertheless be effective in triggering cytotoxic effects due to at least the IL15/IL15 receptor portion and/or Fc portion that activates NK cells (in proximity of the aggregated ALL cells). Moreover, and even without NK cell activation, complement dependent cytotoxic effects may be triggered by the presence of the Fc portion in the chimeric molecule complexes.

Consequently, it should also be appreciated that contemplated chimeric molecule complexes may be administered together with NK cells, and especially NK92 cells and derivatives thereof. For example, suitable NK cells may be autologous NK cells from the patient, and such autologous NK cells may be isolated from whole blood, or cultivated from precursor or stem cells using methods known in the art. Moreover, it should be appreciated that the NK cells need not be autologous, but may also be allogenic or heterologous NK cells. However, in particularly preferred aspects of the inventive subject matter, the NK cells are genetically engineered to achieve one or more desirable traits, are NK92 cells, or derivatives of NK92 cells. For example, in one particularly preferred aspect of the inventive subject matter, the genetically engineered NK cell is a NK92 derivative that is modified to have reduced or abolished expression of at least one killer cell immunoglobulin-like receptor (KIR), which will render such cells constitutively activated (via lack of/reduced inhibition).

NK92 cells exhibit an unusual receptor expression profile, expressing a relatively large number of activating (e.g., NKp30, NKp46, 2B4, NKGD, CD28) receptors. Conversely, NK92 cells also express few inhibitory receptors (e.g., NKGA/B, low levels of KIR2DL4, ILT-2), and lack most of the killer inhibitory receptors (KIRs) clonally expressed on normal NK cells. In addition, NK92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK92 cells also express other molecules implicated immune effector cell regulation (CD80, CD86, CD40L, TRANCE) whose relevance in NK killing is unclear.

Moreover, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one MR will be mutated, deleted, or silenced, and especially contemplated MR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells ('activated natural killer cells).

In another preferred aspect of the inventive subject matter, the genetically engineered NK cell may also be an NK92 derivative that is modified to express the high-affinity Fcγ receptor (CD16). Sequences for high-affinity variants of the Fcγ receptor are well known in the art (see e.g., Blood 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells).

In yet a further aspect of the inventive subject matter, the genetically engineered NK cell may also be genetically engineered to express a chimeric T-cell receptor. In especially preferred aspects, the chimeric T-cell receptor will have a scFv portion or other ectodomain with binding specificity against a tumor associated antigen, a tumor specific antigen, and a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells').

One key function of chimeric molecule complex 100, as contemplated herein, is the activation of an immune response to ALL. Most typically, this is achieved by providing an IL15 portion (preferably human IL15) in association with the alpha chain of the IL15 receptor (preferably human IL15Rα) as components of the chimeric molecule complex. For example, in FIG. 1, chimeric molecule complex 110 has IL15 portion 170 (preferably a superagonist version) bound to the alpha chain of IL-15 receptor 130. It should be appreciated that the so bound IL-15 (as opposed to free IL15) strongly activates cells expressing the beta and gamma chain of the IL-15 receptor, which are, for example, found on cytotoxic T-cells and NK cells.

One contemplated advantage is that this chimeric molecule complex (or dimer as shown in FIG. 2) will advantageously activate NK cells and T-cells, stimulate their proliferation, and even lead to memory NK/T cell formation. Furthermore, IL15 also exerts inhibitory effect of immune suppressor cells, and particularly on Tregs and MDSCs. Viewed from another perspective, contemplated methods as described herein will promote formation of activated and proliferating NK and cytotoxic T-cells, memory NK cells expressing NKG2C, memory T-cells, and T-cells that act like NK cells via their NKG2D properties. It should be appreciated that the IL15 receptor should have a minimum length to enable specific binding of IL15 as is discussed in more detail below (e.g., have no more than 10%, 15%, or 30% loss of binding affinity compared with IL15 receptor wild type). Similarly, it should be appreciated that IL15 can be a native IL15 or a genetically engineered IL15 (e.g., with N72D mutation to so form a superagonist).

Furthermore, it should be recognized that contemplated chimeric molecule complexes have significantly increased persistence (i.e., extended serum half life time), which allows the molecule to perform its functions while delaying degradation in the blood stream. Indeed, it was observed that the Fc portion significantly increased the lifespan of IL15 in circulation as compared to IL15 per se. This provides the chimeric molecule complex with persistence, thus prolonging the activity of the molecule in circulation. Another contemplated benefit, as is discussed in more detail below, is that the Fc portion greatly simplifies purification processes during the preparation of purified chimeric molecule complexes. As already noted above, the Fc portion may include at least an Fc portion of an IgG, IgM, IgA, IgD, or IgE antibody.

It is contemplated that a preferred arrangement of the first fusion protein, from N- to C-terminus, is as follows: first affinity portion, IL15 receptor, Fc portion. However, the first fusion protein may also be arraigned as follows: IL-15 receptor, Fc portion, first affinity portion. Ideally, the second affinity portion is arranged, from N- to C-terminus as follows: second affinity portion, IL15 portion.

With respect to the production of contemplated chimeric molecule complexes and di/multimers, various methods of synthesis are contemplated. For example, and in general, it is contemplated that chimeric molecule complexes can be expressed from one or more nucleic acid in patient cells in vivo, in patient or mammalian production cells (e.g., CHO cells) in vitro, or where desired in other cells such as bacteria, yeast, or non-mammalian cells. Most preferably, the individual components of the fusion proteins (e.g., IL15 or IL15Rα, Fc portion, affinity portions, etc.) are expressed from a recombinant nucleic acid as a single polypeptide, typically with short and flexible linker sequences in between the individual components. However, in less preferred aspects, the individual components can be expressed individually and are then coupled together after expression. Such coupling will typically include use of high-affinity binding pairs such as biotin/avidin, protein A/G, short nucleic acids with sequence complementarity, etc. Most preferably, the fusion protein (components) of the chimeric molecule complex will be co-expressed within the same cell.

For example, contemplated chimeric molecule complexes can be prepared as an anti-CD19 (or anti-CD20 or anti-CD22) scFv/huIL-15N72D fusion protein in complex with (i.e., non-covalently bound to) an anti-CD20 (or anti-CD19 or anti-CD22) scFv/huIL-15RαSu/huIgG1 Fc fusion protein, which may optionally also include an anti-CD3 affinity portion in addition to anti-CD19/20/22 or as a replacement of one of the CD19/20/22 affinity portions. As will be readily appreciated, the affinity portions are preferably scFv, but could also have a BiKE or TriKE configuration.

Suitable sequences for affinity portions may be derived from known antibodies or fragments thereof that bind CD19, CD20, or CD22, including Fab and scFv. For example, suitable known antibodies with anti-CD19 binding include blinatumomab, SGN-CD19A, and taplitumomab paptox (anti-CD19), and suitable known antibodies with anti-CD20 binding include rituximab, afutuzumab, ofatumumab, obinutuzumab, AME-133, FBTA05, ibritumomab tiuxetan, KM3065, ocrelizumab, ocaratuzumab, PRO131921, ublituximab, veltuzumab, (anti-CD20), and suitable known antibodies with anti-CD22 binding include bectumomab, epratuzumab, inotuzumab ozogamicin, moxetumomab pasudotox, and pinatuzumab vedotin. Of course, it should be appreciated that the affinity portions may be directly from the above antibodies. Alternatively, it is contemplated that contemplated affinity portions may be prepared by CDR grafting into the scFv or other affinity portion using methods known in the art (see e.g., *Methods Mol Biol.* 2012;907: 237-45; *Monoclon Antib Immunodiagn Immunother.* 2015 Dec. 1; 34(6): 404-417; or *J Biol Chem.* 2010 Mar. 19; 285(12): 9054-9066). In still further contemplated aspects, scFv or other binders with high specificity and affinity (i.e., $K_D$ equal or less than $10^{-9}M$) to one of CD19, CD20, and CD22 may be derived from phage display or mRNA display following known procedures (see e.g., *Hum Vaccin Immunother.* 2012 Dec. 1; 8(12): 1817-1828; or *Methods.* 2013 Mar. 15; 60(1): 10.1016).

Likewise, with respect to IL15 it is contemplated that all known IL15 sequences are deemed suitable for use herein, and particularly human or humanized IL15. Thus, the term "IL15" as used herein refers to all IL-15 forms (including isoforms, prepro, and pro forms), preferably mammalian, and most preferably human or humanized forms. Moreover, contemplated IL-15 proteins also include mutant forms, and particularly mutants with higher biological activity such as N72D mutant form (see e.g., Zhu et al., J Immunol, 183: 3598-3607, 2009). For example, suitable IL15 sequences can be found under Genbank accession numbers X91233 (Genomic DNA), CH471056 (Genomic DNA), or X94223 (mRNA), AK290619 (mRNA), BC100961 (mRNA), and the protein sequence is known under UniProtKB identifier P40933.

Similarly, with respect to the IL15 receptor it is contemplated that all known IL15 receptor sequences are deemed suitable for use herein. However, especially preferred receptor sequences are high-affinity IL15R alpha chain (IL15Rα) receptors, and particularly human or humanized IL15Rα. Thus, the term "IL15 receptor" as used herein refers to all IL-15 forms (including all isoforms), preferably mammalian, and most preferably human or humanized forms. For example, suitable IL15Rα sequences can be found under Genbank accession number AY316538 (Genomic DNA), CH471072 (Genomic DNA), or CR457064 (mRNA), AK304211 (mRNA), BC121140 mRNA, and the protein sequence is known under UniProtKB identifier Q13261.

As discussed above, the fusion proteins may also comprise an Fc domain of an antibody. Most typically, Fc domains will ultimately be present as a dimer as exemplarily shown in FIG. 2. Moreover, it is generally preferred that immunoglobulin from which the Fc domain is obtained is a mammalian, and most preferably human immunoglobulin, and especially IgG1 and IgG2. Other suitable Fc domains may be derived from different Ig classes (such as IgG, IgA, IgE) or subclasses (e.g., IgG1, IgG2, IgG3, IgA1, IgGA2) or variants thereof (see e.g., WO 97/34631 and WO 96/32478). Fc domains are well known in the art and suitable sequences can be obtained from publically available sources such as GenBank, EMBL, SwissProt, etc.

In a particularly preferred example, a first fusion protein containing IL15Rα (or portion thereof) comprises an anti-CD20 scFv portion coupled via a linker to a hu-IL15RαSu portion coupled via a linker to a hu-IgG1 Fc portion. Such first fusion protein forms a complex (via IL15/IL15Rα binding) with a second fusion protein containing IL15 (or portion thereof) that comprises an anti-CD19 scFv portion coupled via a linker (as discussed below) to a hu-IL15N72D portion. Such complex may then form an antibody-like dimer via interaction and disulfide bond formation of the two Fc portions.

Notably, contemplated Fc fusion proteins will have an in vivo pharmacokinetic profile comparable to that of human IgG with a similar isotype, and as such substantially increase the halflife time (up to 21 days) as compared to IL15 alone. For example, the pharmacokinetics and biological activity of a IL-15 super-agonist (IL15N72D) was dramatically increased by binding the IL15N72D to a IL-15Rα/Fc fusion protein (ALT-803), such that the super agonist complex has at least 25-times the activity of the native cytokine in vivo (see e.g., *Cytokine,* 56: 804-810, 2011). Such advantage is expected to persist where such or similar scaffolds are used to carry one or more affinity portions.

As noted above, contemplated fusion proteins will preferably include a (preferably flexible) peptide linker between each of the individual components complexes. Most typically, suitable linker sequences will include between about 7 to 20 amino acids, and preferably between about 10 to 20 amino acids. In further preferred aspects, suitable linker sequences are preferably flexible to reduce steric hindrance and/or facilitate proper folding/tertiary structure. Thus, linkers may include amino acids with small side chains, such as glycine, alanine and serine, to provide for flexibility (G4S linker). Where desired, such mini-sequences may be repeated to achieve a desired length. However, numerous alternative linker sequences are also deemed suitable and appropriate linkers are known in the art (e.g., Whitlow, M. et al., (1991) *Methods*: A Companion to Methods in Enzymology, 2:97-105). Therefore, most typically a linker sequence is between the affinity portion and the IL15 or IL15Rα, and between the IL15Rα and the Fc portion.

Most preferably, contemplated fusion proteins are encoded on a recombinant nucleic acid, typically with codon usage adapted to the host cell that is used to express the fusion proteins. Moreover, it should be appreciated that the chimeric fusion protein complexes may be produced in vivo or in vitro. Therefore, the recombinant nucleic acid may be part of a viral nucleic acid (e.g., recombinant adenovirus that also encodes one or more neoepitopes or polytopes, optionally with co-stimulatory molecules) or part of a DNA vaccine. Alternatively, the recombinant nucleic acid may be a RNA or DNA that is transfected into a production cell to generate recombinant protein. Preferably, the recombinant nucleic acid is part of a vector for extrachromosomal replication such as a phage, virus, plasmid, phagemid, cosmid, or YAC. In particularly preferred aspects, a DNA plasmid is constructed to encodes the fusion proteins contemplated herein and is used to prepare the complexes in clinically meaningful quantities. To that end, the recombinant nucleic acid can be inserted into an appropriate expression vector (i.e., a vector that contains the necessary elements for the transcription and translation of the inserted protein-coding sequence). A variety of host-vector systems may be utilized to express the protein-coding sequence, including mammalian cell systems infected with a virus (e.g., vaccinia virus, adenovirus, etc.), insect cell systems infected with virus (e.g., baculovirus), microorganisms such as yeast containing yeast vectors, or bacteria transformed with bacteriophage DNA, plasmid DNA or cosmid DNA. Depending on the host-vector system utilized, any one of a number of suitable transcription and translation elements may be used. The fusion proteins described herein are preferably produced by standard recombinant DNA techniques.

Another advantage of contemplated compositions and methods is that the step of purification is greatly simplified because the entire chimeric molecule complex can be pulled out of solution by the binding of the Fc portion to a corresponding affinity protein. Therefore, in preferred embodiments, the Fc portion is ideally long enough to (a) facilitate the isolation of the chimeric molecule complex with any affinity protein that binds to the Fc portion (e.g. Protein A or G), and/or (b) facilitate the binding to the Sudlow II domain in albumin. Thus it is contemplated that in at least some embodiments the chimeric molecule complex can be administered as protein complexes with albumin. It is also contemplated that IL15 can be further coupled to alpha-CD3, cellulose binding protein, and/or oligohistidine for the purpose of easier affinity purification. Alternatively, IL15 could be bound to IL2 or another cytokine portion to further enhance activation capability.

When forming dimers, it is contemplated that first and second chimeric molecule complexes can be made in separate batches as homodimers. The batches can then be combined and a reducing agent can then be added to split the bonds between homodimers so the chimeric molecule complexes dissociate. The reducing agent can then be pulled out (e.g. via dialysis), which will cause chimeric molecule complexes to re-associate, but this time in 1st-1st, 2nd-2nd, and 1st-2nd combinations. Further details and methods of producing fusion proteins based on IL15/IL15Rα are described in WO 2017/205726, which is incorporated by reference herein.

It should further be appreciated that the fusion proteins of the inventive subject matter can be combined with any appropriate pharmaceutically acceptable amount in any quantities, and will generally present in an amount of 1-95% by weight of the total weight of the composition. Contemplated compositions may be provided in a dosage form that is suitable for parenteral (e.g., subcutaneous, intravenous, intramuscular, intravesicular, intratumoral or intraperitoneal) administration route. As will be appreciated, pharmaceutical compositions contemplated herein may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). In addition, the formulations may further include appropriate excipients that, upon administration, release the therapeutic agent in a controlled manner. Examples include single or multiple unit tablet or capsule compositions, oil solutions, suspensions, emulsions, microcapsules, microspheres, molecular complexes, nanoparticles, patches, and liposomes.

Most preferably, however, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 µg compound/kg body weight to about 50 mg compound/kg body weight; or from about 5 mg/kg body weight to about 40 mg/kg body weight or from about 10 mg/kg body weight to about 30 mg/kg body weight; or from about 50 mg/kg body weight to about 20 mg/kg body weight; or from about 100 mg/kg body weight to about 10 mg/kg body weight; or from about 150 mg/kg body weight to about 500 mg/kg body weight. For example, the dose is about 0.01, 0.05, 0.1, 1, 5, 10, 25, 50, 75, 100, 150, 200, 250, 300, 350, 400, 450, 500, 550, 600, 650, 700, 750, 800, 850, 900, 950, or 1,000 mg/kg body weight. Alternatively, doses are in the range of about 5 mg compound/Kg body weight to about 20 mg compound/kg body weight. In another example, the doses are about 0.01, 0.05, 0.1, 1, 5, 8, 10, 12, 14, 16 or 18 mg/kg body weight.

It is contemplated that in preferred embodiments, chimeric molecule complexes will be administered in formulations suitable for injection in therapeutically effective amounts. Therapeutically effective amounts can range from 1 ng to 1,000 mg, from 1 µg to 500 mg, from 100 µg to 100 mg. Solubility co-solvents or detergents can be used to increase the storage stability. Additionally, or alternatively, mixed-phase or two-phase liquid systems can be used. Most preferably, chimeric molecule complexes will be formulated in a liquid carrier ready to use. However, it is contemplated that the chimeric molecule complexes can also be formulated in a dried form for reconstitution, by lyophilization or freeze drying.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A chimeric molecule complex, comprising:
a first fusion protein comprising an Fc domain, an IL15 receptor alpha chain, and a first affinity domain, wherein the first affinity domain specifically binds to a CD molecule selected from CD19, CD20, and CD22; and
a second fusion protein comprising an IL15 domain and a second affinity domain, wherein the second affinity domain specifically binds to a CD molecule selected from CD19, CD20, and CD22; and
wherein the first and second fusion proteins form a complex via the IL15 domain and the IL15 receptor alpha chain, and wherein (i) the IL15 receptor alpha chain and the first affinity domain are coupled to each other via a first binding domain, (ii) the IL15 domain and the second affinity domain are coupled to each other via a second binding domain, or (iii) the IL15 receptor alpha chain and the first affinity domain are coupled to each other via a first binding domain and the IL15 domain and the second affinity domain are coupled to each other via a second binding domain.

2. The molecule complex of claim 1, wherein at least one of the first affinity domain or second affinity domain comprise an scFv.

3. The molecule complex of claim 1, wherein at least one of the first binding domain and the second binding domain comprises at least a portion of one or more of biotin, Protein A, Protein B, and an RNA fragment.

4. The molecule complex of claim 1, wherein at least one of the first and second fusion proteins further comprises an affinity domain that binds to CD3.

5. The molecule complex of claim 1, wherein the Fc domain of the first fusion protein comprises at least a portion of one or more of an IgG, IgM, IgA, IgD, and IgE antibody.

6. The molecule complex of claim 1, forming at least a dimer with at least a second chimeric molecule complex.

7. The molecule complex of claim 6, wherein the second chimeric molecule complex comprises:
a third fusion protein comprising an Fc domain, an IL15 receptor alpha chain, and a third affinity domain, wherein the third affinity domain specifically binds to a CD molecule selected from CD19, CD20, and CD22; and
a fourth fusion protein comprising an IL15 domain and a fourth affinity domain, wherein the fourth affinity domain specifically binds to a CD molecule selected from CD19, CD20, and CD22; and
wherein the third and fourth fusion proteins form a complex via the IL15 domain and the IL15 receptor alpha chain.

8. The molecule complex of claim 7, wherein the third and the fourth affinity domains do not each bind the same CD molecule.

9. The molecule complex of claim 7, wherein at least one of the third and the fourth affinity domain does not bind the same CD molecule with respect to the first and the second affinity domain.

10. The molecule complex of claim 7, wherein at least one of the first, second, third, and fourth affinity domains comprise an scFv.

11. The molecule complex of claim 1, wherein the IL15 receptor alpha chain and the first affinity domain form a single polypeptide.

12. The molecule complex of claim 1, wherein at least one Fc domain of the first and third fusion protein is coupled to an albumin.

13. The molecule complex of claim 1, wherein at least one of the first affinity domain and the second affinity domain is a BiKE or TriKE.

14. The molecule complex of claim 1, wherein at least one of the first affinity domain and the second affinity domain comprises a scFv domain with CDR regions of a therapeutic antibody against one of CD19, CD20, and CD22.

15. The molecule complex of claim 14 wherein the therapeutic antibody is selected from the group consisting of blinatumomab, denintuzumab, rituximab, taplitumomab, afutuzumab, ofatumumab, obinutuzumab, lymphomun, ibritumomab, ocrelizumab, ocaratuzumab, ublituximab, veltuzumab, bectumomab, epratuzumab, inotuzumab, moxetumomab, and pinatuzumab.

16. The molecule complex of claim 1, wherein (i) the IL15 domain comprises an IL15 N72D mutant, (ii) the IL15 receptor alpha chain comprises IL15Rα, or (iii) the IL15 domain comprises an IL15 N72D mutant and the IL15 receptor alpha chain comprises IL15Rα.

17. The molecule complex of claim 1, wherein the IL15 domain and the second affinity domain form a single polypeptide.

18. The molecule complex of claim 11, wherein the IL15 domain and the second affinity domain form a single polypeptide.

* * * * *